(12) United States Patent
Holländer

(10) Patent No.: US 8,372,637 B2
(45) Date of Patent: Feb. 12, 2013

(54) METHOD FOR STABILISING A BIOLOGICAL SAMPLE

(75) Inventor: Vera Holländer, Unna (DE)

(73) Assignee: Qiagen, GmbH, Hilden (DE)

(*) Notice: Subject to any disclaimer, the term of this patent is extended or adjusted under 35 U.S.C. 154(b) by 319 days.

(21) Appl. No.: 12/602,142

(22) PCT Filed: May 29, 2008

(86) PCT No.: PCT/EP2008/056648
§ 371 (c)(1),
(2), (4) Date: May 20, 2010

(87) PCT Pub. No.: WO2008/145710
PCT Pub. Date: Dec. 4, 2008

(65) Prior Publication Data
US 2010/0255524 A1   Oct. 7, 2010

(30) Foreign Application Priority Data
May 31, 2007  (DE) .................. 10 2007 025 277

(51) Int. Cl.
*C12N 5/00* (2006.01)
(52) U.S. Cl. ........... 435/325; 435/260; 435/404; 435/29
(58) Field of Classification Search .............. 435/29, 435/325, 404, 260
See application file for complete search history.

(56) References Cited

U.S. PATENT DOCUMENTS

| | | | |
|---|---|---|---|
| 5,010,184 A | 4/1991 | Merz | |
| 5,300,545 A | 4/1994 | Kazmierczak et al. | |
| 5,965,438 A * | 10/1999 | Kadkade et al. | 435/420 |
| 6,204,375 B1 | 3/2001 | Lader | |
| 6,861,213 B2 | 3/2005 | Oelmuller et al. | |
| 7,270,953 B2 | 9/2007 | Hollander et al. | |
| 2005/0221081 A1* | 10/2005 | Liu et al. | 428/338 |
| 2006/0127375 A1* | 6/2006 | Livesey et al. | 424/93.7 |

FOREIGN PATENT DOCUMENTS

| | | |
|---|---|---|
| EP | 0 578 885 A2 | 1/1994 |
| SU | 813844 B * | 1/1982 |
| WO | WO 02/00599 A1 | 1/2002 |
| WO | WO 02/00600 A1 | 1/2002 |
| WO | WO 2004/072228 A2 | 8/2004 |
| WO | WO 2004/072270 A1 | 8/2004 |

OTHER PUBLICATIONS

Derwent abstract for SU 8138448 (Jul. 6, 1979) downloaded Mar. 17, 2012 on West.*
English Translation of SU 813844 (1982).*

* cited by examiner

*Primary Examiner* — Susan Hanley
(74) *Attorney, Agent, or Firm* — Fanelli Haag & Kilger PLLC

(57) ABSTRACT

The present invention relates to a method of stabilizing a biological sample, having the steps of preparation of a biological sample, and of contacting the biological sample with a composition, having a substance according to the following structural formula:

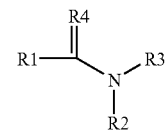

in which R1 is a hydrogen residue or a methyl residue, R2 and R3 are identical or different hydrocarbon residues with a length of the carbon chain of 1-20, and R4 is an oxygen, sulfur or selenium residue (FIG. 1).

13 Claims, 7 Drawing Sheets

METHOD FOR STABILISING A BIOLOGICAL SAMPLE

FIELD OF THE INVENTION

The present invention relates to a method of stabilizing a biological sample, in particular for stabilizing nucleic acids, proteins and the morphology of biological samples.

TECHNICAL BACKGROUND

It has long been known that the genetic origin and the physiological status of a cell can be determined and investigated by studying its genome, its transcriptome, its proteome and its methylome.

The term "genome" denotes the totality of the heritable nucleic acids in a sample, i.e. an organism, a tissue, a cell or a cell compartment or a biopsy, a smear, a section or the like. Generally the heritable nucleic acid is DNA.

The term "transcriptome" denotes the sum of the genes transcribed in such a sample, i.e. transcribed from DNA to RNA, at a given point of time, and thus the totality of all RNA molecules.

The term "proteome" denotes the totality of all proteins in said sample.

The term "methylome" describes the methylation profile of the genome. It comprises the totality and the pattern of the positions of methylated cytosine (mC) of healthy DNA.

Analysis of the genome, transcriptome, proteome and/or methylome is in many respects potentially superior to indirect, conventional methods, e.g. the detection of metabolic products, especially for diagnostic purposes.

In the last twenty years, biological science has developed a comprehensive range of molecular-biological tools for this. In future, therefore, we can expect even wider application of molecular-biological analyses, e.g. in medical and clinical diagnostics, in forensics, in pharmacy in the development and evaluation of medicinal products, in food analysis and in the monitoring of food production, in agriculture in the breeding of useful plants and animals, and in environmental analysis and in many areas of research.

By analyzing the transcriptome, especially the mRNA in cells, the activities of genes can be determined directly. The quantitative analysis of transcript profiles (mRNA profiles) in cells by techniques of modern molecular biology, e.g. real-time reverse-transcriptase PCR ("real-time RT PCR") or gene expression chip analyses makes it possible for example to detect incorrectly expressed genes, so that e.g. metabolic disorders, infections or any predisposition to cancer can be diagnosed.

Analysis of the genome by molecular biomethods, e.g. PCR, RFLP, AFLP or sequencing makes it possible for example to detect genetic defects or to determine the HLA type and other genetic markers. The analysis of genomic DNA and RNA is also employed for the direct detection of infectious pathogens, such as viruses, bacteria etc. Analysis of the methylome provides indications concerning the activity of particular genes; for example, certain methylation profiles allow conclusions to be drawn regarding predisposition to particular diseases.

In particular, the combination of molecular biomethods with morphological methods is very promising. For example, a tissue sample, for which a particular tumor type has been diagnosed morphologically, can be investigated further by characterization of the genome, transcriptome, proteome and/or methylome, in order to determine a tumor subtype, which in its turn makes it possible to initiate targeted therapy.

An essential precondition for the aforementioned investigations is immediate stabilization of the biological sample after removal from its natural environment, i.e. the conservation of its genomic, transcriptomic, methylomic, proteomic and morphological properties that existed at the time of sample collection.

This applies to the hereditary material DNA, and especially to the less stable RNA, which after collection of the biological sample can be broken down very rapidly by the ubiquitous RNAses. The same applies to DNA methylation profiles, which can be lost or can be falsified by environmental effects after sampling.

Furthermore, after collection of a biological sample, e.g. a section, a biopsy or the like, induction of stress genes and the like can also lead to the synthesis of new mRNA molecules, so that the transcription profile of the cells may be altered.

Stabilization of nucleic acids is necessary in particular in the medical field, because in this case nucleic acid-containing samples are often collected, which can only be investigated further after prolonged storage and transport to a laboratory. In the meantime the nucleic acids contained in the samples may change or even decompose completely. This has a massive influence on the result of subsequent tests or makes them completely impossible. Similarly unfavorable conditions occur e.g. in forensics or in sample collection under field conditions.

Stabilization of proteins is also absolutely essential for investigation of the proteome, as proteins are altered very quickly by modification, e.g. phosphorylation and dephosphorylation, and just like nucleic acids, can be degraded specifically or nonspecifically, or neosynthesis may occur after induction.

For the stabilization of nucleic acids and proteins in compact tissue samples there is yet another difficulty, compared with other biological samples. Tissues are compact, multilayered and heterogeneous with respect to composition, contents and structure. For the stabilization of nucleic acids in tissue samples, the stabilizing reagent must act not only on the surface of cells or within a cell layer, but also deep within the compact, multilayered sample material. In addition, it must be possible to address tissue types that are very varied with respect to their contents and morphology. Differences occur for example in cell structure, membrane structure, boundaries/compartmentations and contents, in particular the protein, carbohydrate or fat content.

Stabilization should then take place without the biological sample being destroyed or having to be destroyed for stabilization. Tissue samples in particular, but also cellular samples are often used for morphological investigation in addition to molecular analysis. This should still be possible after stabilization of the sample. Ideally a substance used for stabilization of the genome, transcriptome, proteome and/or methylome also contributes to the stabilization and preservation of morphological-histological integrity.

It must be possible to provide stabilization by very simple and quick handling of the sample, because on the one hand any pretreatment of the sample that is required (e.g. washing or homogenization) prevents the immediate stabilization of the gene expression profile, since during the delay caused by the pretreatment there may for example be degradation or neosynthesis of RNA. On the other hand, any pretreatment and every additional processing step make it more difficult to use the stabilizing agent. Use anywhere that biological samples can be obtained, e.g. in the operating theater, investigations in the field, in a factory producing foodstuffs, at a crime scene, and the like, is only conceivable if the necessary handling is very simple, without requiring equipment and further sample preparation.

PRIOR ART

A form of stabilization of tissue samples including all constituents that is known in the prior art and is very often used, is the freezing or deep-freezing of the samples. For this, the sample is deep-frozen at below −80° C. in liquid nitrogen directly after removal from its natural environment. The sample so treated can then be stored almost indefinitely at about −70° C. and yet remain intact. However, such methods always require very complicated logistic preconditions, as thawing of the samples must be prevented during transport, storage or the very varied processes for application or use. Apart from the additional costs for special sample collecting vessels and for permanent cooling of the samples, in addition the use of liquid nitrogen is not only very complicated, but also requires special precautions.

Furthermore, subsequent analysis of the frozen sample material, especially individual constituents of the sample, is generally very difficult. For example, thawing or partial thawing of the sample during storage, transport or processing leads to the degradation of RNA in particular. Consequently, the thawed or partially thawed samples no longer provide reproducible results. Moreover, further processing, for example dividing up, in particular of pieces of tissue in the frozen state, is very difficult by manual methods or requires increased expenditure on equipment.

Stabilization using formaldehyde solution and subsequent embedding of the stabilized samples, for example in paraffin, for histological investigation of tissues, has also long been known. Nevertheless, such stabilization is generally unsuitable for the application of molecular biomethods, as there is only very inadequate stabilization of nucleic acids, so that at best it can only provide qualitative, but not quantitative detection of the nucleic acids or nucleic acid fragments that are present. Furthermore, stabilization with stabilizing agents that have a crosslinking action, such as formaldehyde solution, leads to reduced extractability of the nucleic acids or proteins from the tissues. In addition, formaldehyde solution is not harmless from the toxicological standpoint.

Preservatives, for example the cationic detergents described in U.S. Pat. No. 5,010,184, U.S. Pat. No. 5,300,545, WO-A-02/00599 and WO-A-02/00600, with which in contrast very good qualitative detection of nucleic acids is possible, are only suitable for samples that contain individual cells or have only one layer of cells. These preservatives are not adequate for stabilization of nucleic acids in compact pieces of tissue.

Furthermore, those reagents and methods by which nucleic acids can be stabilized for qualitative detection are not as a rule also suitable for simultaneous stabilization of proteins, as the biochemical preconditions are different. Moreover, samples stabilized in this way cannot be used for histological investigations, for although the stabilizing agent preserves the nucleic acids for example, it does not preserve the cell or tissue structures.

Other preserving substances, which for example contain highly concentrated ammonium sulfate (see e.g. U.S. Pat. No. 6,204,375), are very suitable for stabilizing nucleic acids in various tissues. Generally, however, they are unsuitable for use in the stabilization of body fluids whether or not they contain cells, e.g. blood, serum or plasma and moreover their stabilization properties are not so good with some tissue types, e.g. adipose tissue. Furthermore, the structural properties e.g. of a tissue sample are lost as a result of treatment with ammonium sulfate; therefore the latter is not suitable for the preservation of histological samples.

Basically, operations with cells or other biological samples cannot necessarily be employed for compact tissues. For the stabilization of nucleic acids in compact tissue samples there is a particular difficulty, compared with other biological samples. With respect to their composition, their contents and structure, tissues are multilayered and heterogeneous. For the stabilization of nucleic acids in compact tissue samples, the stabilizing reagent must act not only on the surface of the cells or within a cell layer, but also deep within the multilayered sample material. Moreover, often within one and the same biological sample, very varied tissue and/or cell types must be addressable, differing for example in cell structure, membrane structure, compartmentations and biomolecules, for example with respect to proteins, carbohydrates and/or fat content.

For reducing the disadvantages in the processing of frozen samples, in particular for the isolation of RNA, so-called transition solutions have also been described. For this, first the frozen tissue is transferred to a solution precooled to −70° C. to −80° C. and is then stored in it for several hours (at least 16 h) at about −20° C. Next, the sample impregnated with the transition solution can only be warmed for a short period, for example at most for dividing up the sample, to working temperatures from −4° C. to 0° C., and possibly up to room temperature, without the nucleic acid status of the sample being changed. However, further analyses and storage of the sample at room temperature are not possible. These transition solutions, known for example from WO-A-2004/72270, mainly consist of monohydric alcohols.

As a disadvantage, the samples treated with common transition solutions only remain stable for a very short time at room temperature, so that the time available for processing is quite meager and is very easily exceeded, especially when processing many samples, in particular with cutting and weighing operations. Furthermore, transition takes place very slowly, so that experiments cannot follow directly, with waiting times generally of one day. The samples thus treated can also not be transported at room temperature and remain intact, because not only the transition, but also the subsequent stable storage of the sample must take place at temperatures of ≦−20° C. In addition the sample can only be transported at ≦−20° C., necessitating the use of refrigerants, for example dry ice, during transport. Furthermore, it should be noted that the monohydric alcohols, such as methanol, ethanol or isopropanol, used in WO-A-2004/72270 are flammable, volatile or toxic, and therefore require special safety precautions when they are used.

Use of the conventional transition solutions does offer improvements in the processing of samples, e.g. weighing or cutting to size, but they neither reduce the costs of equipment (as the solution for transition must be precooled at −70 to −80° C. and therefore appropriate refrigerating equipment must still be available), nor can the samples treated with the transition solution be stabilized at room temperature for an extended period of time.

It is clear from the foregoing that it is difficult to stabilize on the one hand the genome, the transcriptome, the proteome and the methylome (thus DNA, RNA, proteins and the methylation profile) simultaneously in a biological sample, and on the other hand the histological-morphological state of the sample, at low cost. For example, in order to protect a sample against RNA degradation by the ubiquitous RNAses, it would be sensible to denature all enzymes in the medium (and therefore also all RNAses). However, this would run counter to the aforementioned objective, as this would massively impair the proteome. The same would apply if we were to try to denature the proteases, to prevent protease-mediated protein degradation. Conversely, a measure that leaves the proteome of a sample as intact as possible, also protects the ubiquitous RNAses, so that there is a risk of impairing the transcriptome.

The problem to be solved by the present invention

The present invention is based on the problem of overcoming the disadvantages arising from the prior art, described above.

Furthermore, the present invention is based on the problem of providing a method of stabilizing a biological sample, with which both frozen and fresh biological samples can be stabilized under temperature conditions that are as moderate as possible, for example even at room temperature, without impairing the genome, transcriptome, proteome, metabolome and methylome or the histological-morphological state of the biological sample.

Furthermore, the method of stabilizing a biological sample should also permit analysis of the biomolecules contained in the biological sample. In this connection, the method of stabilization should in particular make it possible for both proteins and nucleic acids to be analyzed qualitatively and quantitatively in the stabilized biological sample. Moreover, the quality of the nucleic acids, which can for example be determined by gel analysis or by the number of PCR cycles to reach a specified amount of nucleic acid, and the quality of the proteins, which for example in the case of an enzyme can be determined by Western blot analyses and optionally by appropriate activity tests, should be impaired only slightly, or not at all, by the stabilization of the biological sample.

Furthermore, the method of stabilizing a biological sample should result in a stabilized biological sample that not only can be analyzed at moderate temperatures, for example at room temperature, but optionally can be stored before or after such an analysis for as long as possible under said moderate temperature conditions.

In the case of biomolecules, the term "stabilization" preferably means the inhibition of the decomposition, modification, induction or change in the activity of biomolecules. In the case of histological analyses of biological samples, the term "stabilization" preferably means prevention of a substantial change in the morphology of the samples.

SUMMARY OF THE INVENTION

This problem is solved by the features presented in the main claim. The subclaims present preferred embodiments. It should be noted that the stated ranges are always to be understood as including the respective limit values.

Accordingly it is proposed to provide a method of stabilizing a biological sample that has the following steps:
a) preparation of a biological sample, and
b) contacting the biological sample with a composition having a substance according to the following structural formula:

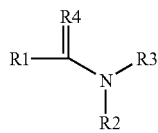

in which R1 is a hydrogen residue or a methyl residue, R2 and R3 are identical or different hydrocarbon residues with a length of the carbon chain of 1-20, and R4 is an oxygen, sulfur or selenium residue.

The hydrocarbon residues R2 and/or R3 can be selected independently of one another from the group comprising alkyl, long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. General groups, for instance alkyl, alkoxy, aryl etc. are claimed and described within the description and the claims. Unless stated otherwise, preferably the following groups are used within the generally described groups within the scope of the present invention:

alkyl: linear and branched C1-C5 alkyls,
long-chain alkyls: linear and branched C5-C20 alkyls
alkenyl: C2-C6 alkenyl,
cycloalkyl: C3-C8 cycloalkyl,
alkoxy: C1-C6 alkoxy,
long-chain alkoxy: linear and branched C5-C20 alkoxy,
alkylenes: a divalent linear or branched aliphatic, cycloaliphatic or aromatic hydrocarbon residue with 2 to 18 carbon atoms optionally containing heteroatoms, e.g. selected from the group comprising: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; 1,4-pentylene, 1,6-hexylene, 1,7-heptylene, 1,8-octylene, 1,9-nonylene, 1,10-decylene, 1,11-undecylene, 1,12-docedylene, cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl
alkenediyl: selected from the group comprising: 1,2-propenediyl, 1,2-butenediyl, 2,3-butenediyl, 1,2-pentenediyl, 2,3-pentenediyl, 1,2-hexenediyl, 2,3-hexenediyl, 3,4-hexenediyl
alkynediyl: is equal to —C≡C—,
aryl: selected from aromatics with a molecular weight below 300 Da,
arylenes: selected from the group comprising: 1,2-phenylene; 1,3-phenylene; 1,4-phenylene; 1,2-naphthalenylene; 1,3-naphthalenylene; 1,4-naphthalenylene; 2,3-naphthalenylene; 1-hydroxy-2,3-phenylene; 1-hydroxy-2,4-phenylene; 1-hydroxy-2,5-phenylene; and 1-hydroxy-2,6-phenylene,
carboxylate: the group —C(O)OR, where R is selected from: hydrogen; C1-C6 alkyl; phenyl; C1-C6 alkyl-C6H5; Li; Na; K; Cs; Mg; and Ca,
carbonyl: the group —C(O)R, where R is selected from: hydrogen; C1-C6 alkyl; phenyl; C1-C6 alkyl-C6H5 and amine (resulting in an amide) selected from the group: —NR'2, where each R' is selected independently from: hydrogen; C1-C6 alkyl; C1-C6 alkyl-C6H5; and phenyl, where, if both Rs represent C1-C6 alkyl, they can form an NC3 to NC5 heterocyclic ring, with alkyl substituents of the ring forming the other alkyl chain,
alkylsilyl: the group —SiR$_1$R$_2$R$_3$, where R$_1$, R$_2$ and R$_3$ are selected independently of one another from: hydrogen; alkyl; long-chain alkyl, phenyl, cycloalkyl, haloalkyl, alkoxy, long-chain alkoxy,
alkylsilyloxy: the group —O—SiR$_1$R$_2$R$_3$, where R$_1$, R$_2$ and R$_3$ are selected independently of one another from: hydrogen; alkyl; long-chain alkyl, phenyl, cycloalkyl, haloalkyl, alkoxy, long-chain alkoxy.

It should be emphasized, however, that the hydrocarbon residues R2 and/or R3 are especially preferably alkyl residues and/or long-chain alkyl residues according to the above definition.

Moreover, the chain length of these hydrocarbon residues has various effects, which will be discussed below.

Firstly, the chain length has an influence on the permeation of the composition according to the invention into the sample; with large chain lengths, permeation is slower for steric reasons; however, there are indications that the preserving effect of compositions with large chain lengths is longer-lasting.

In the case of samples in suspension (e.g. blood samples, urine, smears etc.) the problem of permeation is less acute, as the diffusion paths are far shorter here, and so even substances according to the invention with very large chain lengths on R2 and/or R3 proceed sufficiently quickly to all regions that are to be preserved.

Furthermore, with very large chain lengths on R2 and/or R3, so that the substance is in the form of a solid, a solvent can be added to the composition according to the invention in order to dissolve the substance and thus make it accessible for preservation of the sample.

Alternatively the substance can also be used as a solid and can be dissolved directly in a liquid sample.

Very large chain lengths on R2 and/or R3 lead on the other hand optionally to greater hydrophobicicity of the composition according to the invention and can for example promote the permeation—and thus the preservation—of fat-rich or lipid-rich samples; with such samples, however, compositions according to the invention with small chain lengths on R2 and/or R3 sometimes have permeation problems.

Based on the foregoing, a person skilled in the art will, according to the particular requirements, intentionally select the chain lengths on R2 and/or R3, without performing an inventive step. This may be required in routine experiments, for determining the dissolution behavior, permeation and suitability for preservation of the substances selected in each case. Regarding the suitability for preservation, a person skilled in the art will find, in the examples of the present invention, comprehensive information on how this property can be investigated.

The chain length n on R2 and/or R3 can in particular have the values 1, 2, 3, 4, 5, 6, 7, 8, 9, 10, 11, 12, 13, 14, 15, 16, 17, 18, 19 and 20.

Preferably R2 and R3 have lengths of the carbon chain of 1-10. In this case the chain length n can in particular have the values 1, 2, 3, 4, 5, 6, 7, 8, 9, and 10.

Especially preferably, R2 and R3 have lengths of the carbon chain of 1-5. In this case the chain length n can in particular have the values 1, 2, 3, 4 and 5.

Especially preferably, however, in particular methyl and ethyl residues are used on R2 and/or R3. The chain length n then has values of 1 and 2.

Basically it should be pointed out that the substance used in the composition according to the invention can be used as the sole agent for preservation. The substance can also be used in conjunction with other preserving substances or even only as an additive to other preserving substances in the composition. The term "other preserving substances" is to be understood here in particular as mono- and/or polyhydric alcohols, aromatic alcohols, salts and salt solutions, crosslinking agents, cationic detergents and other reagents known by a person skilled in the art, as well as the preserving substances stated in the examples. Other preserving substances are mentioned in the text.

The volume ratio or weight ratio between the substance according to the invention and one or more other preserving substances in the composition according to the invention can be in the range from 0.01:100 to 100:0. Preferably it is in the range from 0.1:100 to 100:0 and especially preferably it is in the range from 1:100 to 100:0 and particularly preferably it is in the range from 5:100 to 100:0.

Regarding the volume ratio or weight ratio between the composition according to the invention and the sample to be preserved, there are various cases to be considered.

For the case when the composition according to the invention is in liquid form and the sample to be preserved is in solid form, it is for example envisaged to add 100 mg of sample to 0.1-1 ml of composition according to the invention. There is no technically based maximum volume of addition, which is therefore rather based on practical considerations (e.g. vessel size).

However, for the case when the composition according to the invention is in solid/crystalline form and the sample to be preserved is in liquid form (e.g. blood sample), much smaller volume or weight ratios can be used; these are for example in the range from 5:1 to 1:1000.

The proportion of the required composition according to the invention naturally also depends on the amount of material to be preserved. For example, since a urine sample contains mainly water, which does not require preservation, the proportion of the composition according to the invention can be very much smaller than when for example a tissue sample containing much cellular material is to be preserved.

The class of substances used according to the invention is for example dialkylacetamides (if R1 is a methyl residue) or dialkylformamides (if R1 is a hydrogen residue). These substances are polar solvents, which find application in particular in plastics and fiber technology. In connection with biological applications, however, only the use of N,N-dimethylacetamide is known, for induction of the differentiation of erythroid cells (M. Tanaka et al. (1975), "Induction of erythroid differentiation in murine virus infected erythroleukemia cells by highly polar compounds." PNAS, 72, 1003), but not the suitability of these substances for the stabilization of biological samples.

The inventors have the distinction of being the first to recognize that these substances are also suitable for the stabilization of biological samples. This finding is all the more surprising as the existing fields of application of these substances would have made such use seem unlikely.

So far the inventors can only speculate as to the mechanism of action with reference to sample preservation. However, based on experimental findings it must be regarded as certain that although in particular the dialkylformamides coming under the above definition have structural similarities with the fixatives formaldehyde and acetaldehyde, unlike what happens with the latter, no fixing or crosslinking of the macromolecules occurs.

It is preferred if the biological sample is a frozen biological sample. Such samples are available in large numbers e.g. in gene and tissue banks; their further analysis would profit enormously from the method according to the invention. This is of interest in particular for the epidemiological analysis of older samples, but also for forensics, archaeology and the like. However, the sample can also be a non-frozen biological sample. The advantages of the invention are especially useful here, as expensive refrigerating equipment can be dispensed with, for stabilizing a sample immediately after it is obtained. This is also of great advantage for the fields of application already mentioned.

Especially preferably, the biological sample is a material selected from the group comprising sample material, plasma, body fluids, blood, serum, cells, leukocyte fractions, crusta phlogistica, sputum, saliva, urine, semen, feces, forensic samples, smears, aspirates, biopsies, tissue samples, tissue parts and organs, food samples, environmental samples, plants and plant parts, bacteria, viruses, viroids, prions, yeasts and fungi, and fragments or constituents of the aforementioned materials, and/or isolated, synthetic or modified proteins, nucleic acids, lipids, carbohydrates, metabolic products and/or metabolites.

The substance used according to the invention is preferably a substance selected from the group comprising N,N-dimethylacetamide, N,N-diethylacetamide, N,N-dimethylformamide, N,N-diethylformamide, N,N-dimethylthioformamide and N,N-diethylthioformamide. Their structural formulas are as follows:

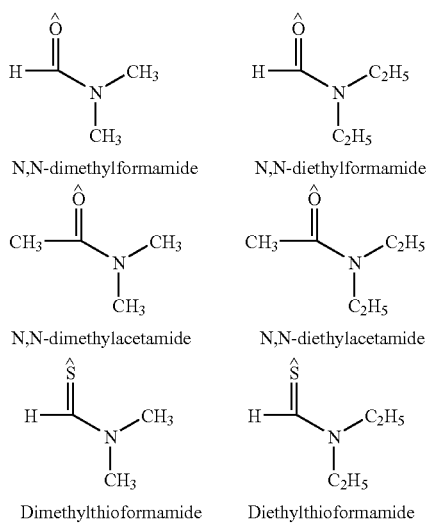

Furthermore it is envisaged according to the invention that the sample is in addition brought in contact with one or more substances selected from the group comprising mono- and/or polyhydric alcohols, solvents, fixatives, buffer substances, osmotically active substances, chelators, reducing agents, agents for improving the visibility of the cell nucleus, crosslinking substances as formaldehyde, p-formaldehyde, acetaldehyde or glutaraldehyde and salts, for example chaotropic salts, organic salts, and inorganic salts, in particular salts of alkali metals and alkaline-earth metals and ammonium salts.

Especially preferred substances are in particular mono- and polyhydric alcohols, organic acids such as acetic acid, alcohols such as methanol and ethanol, acetone, DMSO and guanidine-isothiocyanate buffers.

In a preferred embodiment it is envisaged that the contacting of the biological sample with the composition takes place at a temperature in the range from −80° C. to +80° C. Preferably the contacting of the biological sample with the composition takes place at a temperature in the range from 0° C. to +80° C. Further preferred ranges are the ranges from 8° C. to +80° C., 18° C. to +80° C. and room temperature to +80° C. Under certain conditions the ranges from 30° C. to +80° C., 50° C. to +80° C. or 60° C. to +80° C. may also be preferred.

The formulation that the "contacting of the biological sample with the composition takes place at a temperature in the range from −80° C. to +80° C." or at another of the temperatures stated above, means that after the contacting of the biological sample with the composition, the temperature of the mixture so obtained lies within the range of temperatures stated above. For example, it is possible that a sample deep-frozen to temperatures below −20° C., for example a sample stored in liquid nitrogen, is used as the biological material, and in this case such an amount of composition or a composition with such a temperature is used, so that after the contacting of the deep-frozen biological sample with the composition, the temperature of the mixture (and therefore also the temperature of the biological sample) is in the aforesaid temperature range.

Furthermore, according to a special embodiment of the method according to the invention it may also be preferable for the biological sample, after the contacting with the composition, preferably under the temperature conditions stated above, then to be stored at a temperature in the range from −80° C. to +80° C., preferably in the range from 0° C. to +80° C., still more preferably in the range from 2° C. or 8° C. to +80° C. and even more preferably in the range from 18° C. to +80° C. or room temperature, and said storage can take place for a period of time of at least one day, preferably at least 2 days, even more preferably at least 3 days, optionally for at least one week, at least two weeks, at least one month, at least three months, at least six months or even at least 12 months.

The method according to the present invention makes it possible for a treated biological sample to be stored at room temperature, at refrigerator temperatures or at even higher temperatures, without any discernible degradation of biomolecules such as nucleic acids, proteins or metabolites in the biological sample. This represents a significant advantage over conventional methods of stabilization, as the method can be carried out without the use of liquid nitrogen or of freezing equipment and the stabilized sample can also be stored without the use of liquid nitrogen or of freezing equipment. This is a particular advantage especially in regions lacking infrastructure, and therefore makes the method interesting e.g. for epidemiological investigations in developing countries, for paleontological and archaeological investigations, for investigations in the field or for forensics.

After the treatment according to the invention and optionally before or also after a possible storage step, the treated biological sample can also be embedded in suitable embedding media, for example in paraffin or the like, so that tissue sections suitable for histological investigations can be prepared more easily from the biological sample.

Furthermore, according to a special embodiment of the method according to the invention it may be preferable for the aforementioned steps to be followed by the step of histological-morphological analysis of the biological sample brought in contact with the composition and/or the step of analysis of biomolecules in or from the biological sample brought in contact with the composition, and said step can optionally also be carried out before or after storage according to the step described above.

"Histological analysis" preferably means any method of investigation that is suitable for analyzing the morphological state of a tissue, a tissue section, a cell or subcellular structures, for example by microscopy and optionally using staining or labeling techniques known by a person skilled in the art.

For histological-morphological analysis it can in particular also be envisaged to add suitable dyes or labeled antibodies to specified constituents of the sample, for example tumor markers or the like, to the sample before the analysis. The analysis is carried out e.g. using light, fluorescence or video microscopy. The histological-morphological methods used for this, in particular cutting, labeling and staining techniques and immunohistochemical techniques, are known or can easily be found by a person skilled in the art from the relevant literature.

In the analysis of biomolecules, a genomic, proteomic, metabolomic, transcriptomic or methylomic analysis can be envisaged. The molecular biomethods used in each case, in particular amplification, sequencing and detection techniques, are known or can easily be found by a person skilled in the art from the relevant literature.

All biomolecules known by a person skilled in the art can come into consideration as biomolecules that are to be analyzed, in particular natural, modified or synthetic nucleic acids, natural, modified or synthetic proteins or oligopeptides, hormones, growth factors, metabolic substrates, lipids, oligosaccharides or proteoglucans. All nucleic acids known by a person skilled in the art come into consideration as nucleic acids, in particular ribonucleic acids (RNA), for example mRNA, siRNA, miRNA, snRNA, t-RNA, hnRNA or ribozymes, or deoxyribonucleic acids (DNA). Basically it can be any type of polynucleotide representing an N-glycoside or C-glycoside of a purine or pyrimidine base. The nucleic acid can be single-stranded, double-stranded or multistranded, linear, branched or circular. It can correspond to a molecule occurring in a cell, such as genomic DNA or messenger RNA (mRNA), or can be produced in vitro such as complementary DNA (cDNA), antisense RNA (aRNA), or synthetic nucleic acids. The nucleic acid can consist of a few subunits, at least two subunits, preferably eight or more subunits, such as oligonucleotides, several hundred subunits and up to several thousand subunits, such as certain expression vectors, or considerably more subunits, such as genomic DNA. Preferably the nucleic acid contains the coding information for a polypeptide functionally related to regulatory sequences, which permit the polypeptide to be expressed in the cell in which the nucleic acid is inserted or in which it occurs naturally. Thus, in a preferred embodiment the nucleic acid is an expression vector. In another embodiment it is a pDNA (plasmid DNA), a siRNA, a siRNA duplex or a siRNA heteroduplex, the term "siRNA" meaning ribonucleic acids with a length of about 22 nucleotides, which result from cleavage of a double-stranded RNA (dsRNA) by the enzyme "Dicer" and are incorporated in the "RISC" (RNA-induced silencing complex) enzyme complex. Other biomolecules according to the above definition include in particular metabolites and metabolic products.

The formulation "analysis of biomolecules in or from the biological sample brought in contact with the composition" means that the analysis can take place both in situ and ex situ, for example after isolation of the biomolecules from the biological sample. If biomolecules are to be isolated from a biological sample for the purpose of analysis, it may be advantageous, especially in the case of cells, tissues or other complex or compact samples, to homogenize the samples first, and this homogenization can be carried out mechanically, for example by means of cannulas, mortars, rotor-stator homogenizers, a ball mill or the like, chemically using suitable lysis buffers, which usually contain detergents and/or chaotropic substances, enzymatically, for example using proteases, or by a combination of these measures.

For histological analysis or for the analysis of biomolecules in or from the biological sample, all methods of analysis known by a person skilled in the art and appearing to be suitable can be used, preferably methods selected from the group comprising light microscopy, electron microscopy, confocal laser scanning microscopy, laser micro-dissection, scanning electron microscopy, Western blotting, Southern blotting, enzyme-linked immunosorbent assay (ELISA), immunoprecipitation, affinity chromatography, mutation analysis, polyacrylamide gel electrophoresis (PAGE), in particular two-dimensional PAGE, HPLC, polymerase chain reaction (PCR), RFLP analysis (restriction fragment length polymorphism analysis), SAGE analysis (serial analysis of gene expression), FPLC analysis (fast protein liquid chromatography), mass spectrometry, for example MALDI-TOFF mass spectrometry or SELDI mass spectrometry, microarray analysis, LiquiChip analysis, analysis of the activity of enzymes, HLA typing, sequencing, WGA (whole genome amplification), WTA (whole transcriptome amplification), RT-PCR, real-time PCR or –RT-PCR, RNase protection analysis or primer-extension analysis.

As already mentioned, the combination of histological-morphological findings with findings from molecular-biological analysis is particularly promising for some usage scenarios, for example tumor diagnosis or the diagnosis of neurodegenerative diseases. According to a special embodiment of the method according to the invention, the relevant step therefore comprises both a histological analysis of the biological sample and an analysis of biomolecules in or from the biological sample. According to another special embodiment of the method according to the invention the relevant step comprises both an analysis of nucleic acids in or from the biological sample and an analysis of proteins in or from the biological sample.

A kit of parts, having the composition according to the invention, is also envisaged according to the invention. Preferably said kit can also contain an optionally sealable vessel for sample collection, preparation and/or storage, and/or reagents for the analysis of biomolecules in or from a biological sample or for analysis of the morphology of a biological sample. Reagents that may be considered for the analysis of biomolecules include in particular reagents for the detection and quantification of DNA, RNA, proteins and methylated nucleotides. A person skilled in the art can locate such reagents from the technical literature without an inventive step on his part. Often such reagents can be obtained ready for use as kits for the biomolecules that are to be analyzed in each case. These reagents comprise in particular dyes for staining cells or cell constituents, antibodies, optionally labeled with fluorescent dyes or enzymes, an absorption matrix, such as DEAE cellulose or a silica membrane, substrates for enzymes, agarose gels, polyacrylamide gels, solvents such as ethanol or phenol, aqueous buffer solutions, RNase-free water, lysis reagents, alcoholic solutions and the like.

A sample collecting vessel can already contain the composition. It is also conceivable, however, for the kit to include, as another component part, a metering device that is filled with the composition and by means of which defined portions of the composition can be introduced into the vessel, preferably under sterile conditions. Said metering device can for example be constructed in the form of a soap dispenser.

The invention also includes the use of one of the compositions described above or of the kit in a method of treatment of a biological sample. A method of analysis of a biological sample is also envisaged according to the invention, using a kit as described above or a composition as described above.

The present invention is explained in more detail by the examples and drawings presented and discussed below. It should be noted that the examples are only of a descriptive character and are not intended to limit the invention in any way.

EXAMPLE 1

Transition with Various Solutions According to the Invention

Figure 1:
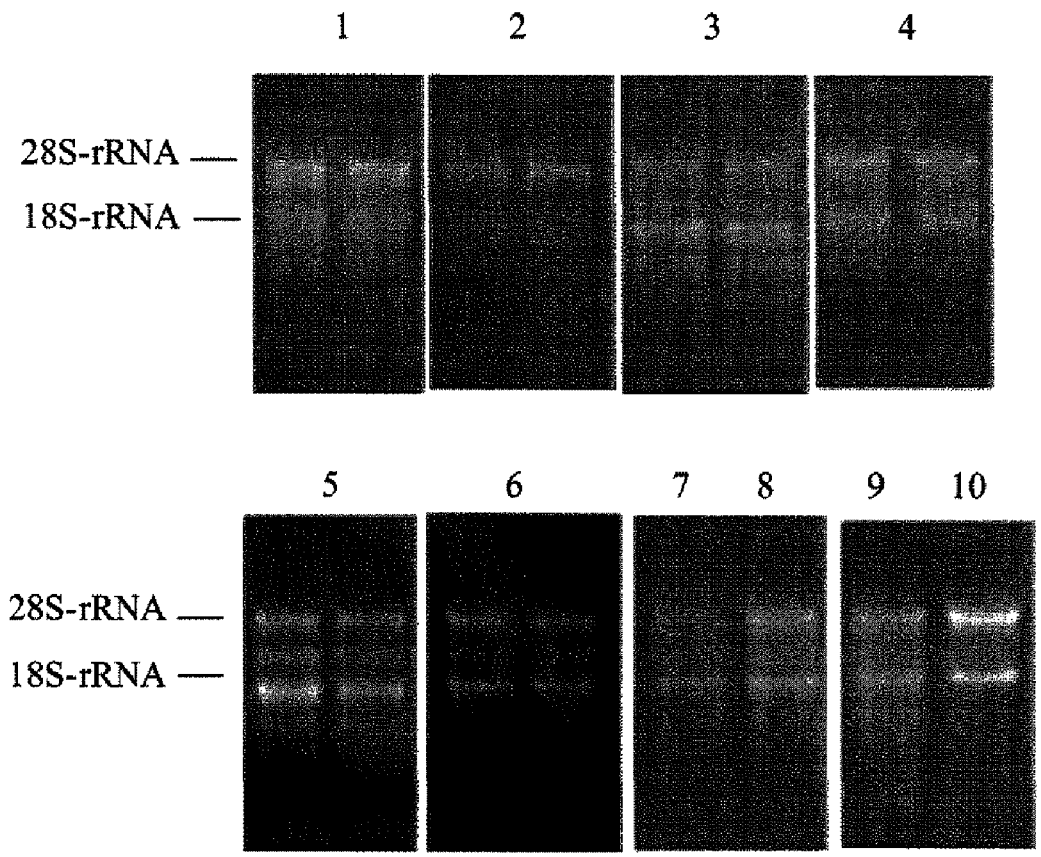
FIG. 1 shows the stabilization of RNA in rat liver tissue treated with N,N-dimethyl acetamide alone and with other solvents.

Rat liver tissue, which was frozen in liquid nitrogen after collection and was stored at −80° C., is used for this test. For each transition experiment, 20 to 50 mg of tissue is weighed and frozen, various undiluted and non-cooled solutions (see Table 1) are added and the sample is stored for 3 days at 2-8° C. in the refrigerator and for one day and optionally 3 days at room temperature. Following transition, the tissue is taken out of the transition solution. For RNA isolation, 350 µl of a commercially available guanidinium isothiocyanate buffer, e.g. RLT buffer from the company QIAGEN, is added per 10 mg of tissue. The sample is homogenized by means of a ball mill, e.g. MM300 from QIAGEN, for a period of 5 min at 20 Hz with 5 mm steel balls, during which the guanidinium isothiocyanate buffer lyses the cells in a manner known from the prior art and denatures the proteins that are released. Then the lysates are centrifuged at 14000 rev/min for 3 min. Two portions each of 350 µl, representing the equivalent of 10 mg tissue, are withdrawn from the supernatant. 1 volume (350 µl) of 70% ethanol is added to these samples, mixing by repeated pipetting or by vortexing for a period of approx. 5 s. The lysate is then applied in a commercially available spin column containing silica membrane, e.g. RNeasy columns from QIAGEN, and is driven through the membrane by centrifugation (1 min at 10 000×g). The RNA remains bound to the membrane and is then washed with a first commercially available washing buffer containing guanidinium isothiocyanate, for example with buffer RW1 from QIAGEN, and then with a second washing buffer containing Tris or Tris and alcohol, e.g. buffer RPE from QIAGEN. During this, the washing buffers are in each case driven through the membrane by centrifugation (1 min at 10 000×g). Washing with the second washing buffer containing Tris or Tris and alcohol is repeated with a smaller volume, simultaneously drying the membrane by centrifugation (2 min at max. rpm, here 20 000×g). For elution, 40 µl of RNase-free water is pipetted onto the membrane, to remove the purified RNA from the membrane. After incubation for 1 min at a temperature in the range 10-30° C., the eluate is driven through the membrane by centrifugation (1 min at 10 000×g) and the elution step is repeated once more for the purpose of complete elution. The amount of total RNA isolated is determined, after dilution in water, by photometric measurement of the absorption of light at a wavelength of 260 nm. The quality of the RNA thus obtained is determined by photometric determination of the ratio of light absorption at 260 nm to that at 280 nm. The results of the isolation operations are shown in Table 1. The mean values of the determination in duplicate are given in each case.

TABLE 1

RNA yield and quality according to photometric measurement

| Transition solution | Storage | OD260/OD280 | RNA yield/µg |
|---|---|---|---|
| N,N-Dimethylacetamide | 3 d 2-8° C. | 1.88 | 63.2 |
|  | 1 d RT | 1.88 | 61.9 |
| N,N-Diethylacetamide | 3 d 2-8° C. | 1.85 | 59.2 |
|  | 1 d RT | 1.85 | 59.1 |
| N,N-Diethylformamide | 3 d 2-8° C. | 1.79 | 47.8 |
|  | 1 d RT | 1.78 | 46.1 |
|  | 3 d RT | 1.80 | 55.6 |
| Dimethylthioformamide | 3 d 2-8° C. | 1.82 | 66.4 |
|  | 1 d RT | 1.79 | 47.1 |
|  | 3 d RT | 1.80 | 43.0 |

The results show that the solutions according to the invention can be used successfully for the stabilization of RNA in transition experiments.

EXAMPLE 2

Transition with Mixtures with N,N-dimethylacetamide

Rat liver tissue, which was frozen in liquid nitrogen after collection and then stored at −80° C., is used for this test. For each transition experiment, 20 to 50 mg of tissue is weighed and frozen, various non-cooled solutions (see Table 2) are added and the samples are stored for 3 days at 25° C. Following transition, the RNA is isolated as described in example 1.

The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 2. The mean values of determination in duplicate are given in each case.

TABLE 2

RNA yield and quality according to photometric measurement

| Transition solution | Storage | OD260/OD280 | RNA yield/µg |
|---|---|---|---|
| 75% N,N-Dimethylacetamide + 25% DMSO | 3 d 25° C. | 1.71 | 21.9 |
| 75% N,N-Dimethylacetamide + 25% acetone | 3 d 25° C. | 1.75 | 39.1 |
| 50% N,N-Dimethylacetamide + 50% acetone | 3 d 25° C. | 1.74 | 36.2 |
| 25% N,N-Dimethylacetamide + 75% acetone | 3 d 25° C. | 1.76 | 52.9 |
| 75% N,N-Dimethylacetamide + 25% methanol | 3 d 25° C. | 1.73 | 44.5 |
| 50% N,N-Dimethylacetamide + 50% methanol | 3 d 25° C. | 1.76 | 51.7 |
| 25% N,N-Dimethylacetamide + 75% methanol | 3 d 25° C. | 1.80 | 54.1 |

TABLE 2-continued

RNA yield and quality according to photometric measurement

| Transition solution | Storage | OD260/OD280 | RNA yield/µg |
|---|---|---|---|
| 75% N,N-Dimethylacetamide + 25% diethylene glycol | 3 d 25° C. | 1.80 | 27.0 |
| 25% N,N-Dimethylacetamide + 75% diethylene glycol | 3 d 25° C. | 1.77 | 20.8 |

The results show that the reagents according to the invention can also be used successfully in mixtures with other reagents, such as mono- and/or polyhydric alcohols, DMSO or aldehydes.

EXAMPLE 3

Transition with Mixtures of N,N-dimethylacetamide and Phenol

Rat liver tissue, which was frozen in liquid nitrogen after collection and then stored at −80° C., is used for this test. For each transition experiment, 20 to 50 mg of tissue is weighed and frozen, various non-cooled mixtures of N,N-dimethylacetamide and phenol (see Table 3) are added and the samples are stored for 3 days at room temperature. Following transition, the RNA is isolated as described in example 1.

The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 3. The mean values of determination in duplicate are given in each case.

TABLE 3

RNA yield and quality according to photometric measurement

| Transition solution | Storage | OD260/OD280 | RNA yield/µg |
|---|---|---|---|
| N,N-Dimethylacetamide + 10% phenol | 3 d RT | 1.77 | 40.1 |
| N,N-Dimethylacetamide + 20% phenol | 3 d RT | 1.77 | 38.7 |
| N,N-Dimethylacetamide + 30% phenol | 3 d RT | 1.80 | 51.2 |
| N,N-Dimethylacetamide + 45% phenol | 3 d RT | 1.80 | 41.6 |

The results show that solutions according to the invention can also be used successfully for transition with phenol as additive.

EXAMPLE 4

Use of N,N-dimethylacetamide as Additive for Improving Stabilization Properties

Rat liver tissue, which was frozen in liquid nitrogen after collection and then stored at −80° C., is used for this test. For each transition experiment, 20 to 50 mg of tissue is weighed and frozen, various non-cooled solutions are added and the sample is stored for 3 days at 2-8° C. in the refrigerator or for 1 day at room temperature (see Table 4). Following transition, the RNA is isolated as described in example 1. The RNA isolated is analyzed on agarose gels stained with ethidium bromide. For this, for example 1.0% formaldehyde-agarose-MOPS gels are prepared. In each case, 5 µl of the eluate is used.

TABLE 4

| No. | Transition solution | Storage |
|---|---|---|
| 1 | 100% diethylene glycol | 3 d 2-8° C. |
| 2 | 95% diethylene glycol + 5% N,N-dimethylacetamide | 3 d 2-8° C. |
| 3 | 100% triethylene glycol | 1 d RT |
| 4 | 95% triethylene glycol + 5% N,N-dimethylacetamide | 1 d RT |
| 5 | 100% 1,2,3-propanetriol | 3 d 2-8° C. |
| 6 | 95% 1,2,3-propanetriol + 5% N,N-dimethylacetamide | 3 d 2-8° C. |
| 7 | 100% 1,5-pentanediol | 1 d RT |
| 8 | 100% 1,5-pentanediol | 3 d 2-8° C. |
| 9 | 95% 1,5-pentanediol + 5% N,N-dimethylacetamide | 1 d RT |
| 10 | 95% 1,5-pentanediol + 5% N,N-dimethylacetamide | 3 d 2-8° C. |

The results are presented in FIG. 1. Gels 2, 4, 6, 9 and 10 contain samples to which N,N-dimethylacetamide and optionally other preserving substances were added, whereas the other gels contain untreated samples or samples only treated with other preserving substances. It can be seen that here, in comparison with the other gels (1, 3, 5, 7 and 8), the RNA content is higher and in particular the quality of the RNA is better. RNA degradation can be seen in gel analyses from the decrease in 28SrRNA compared with 18SrRNA. The native ratio of 28SrRNA to 18SrRNA is about 2:1. As degradation progresses, the ratio of these two rRNA bands changes to 1:1, later to 1:2, and subsequently to complete disappearance of the 28SrRNA bands and later also of the 18SrRNA bands. Moreover, when there is RNA degradation, other bands may also become visible in the gel, relating to rRNA degradation products of a specific size. In addition, RNA degradation leads to the appearance of a low-molecular "smear", consisting of degraded RNA fragments, which becomes visible in particular in the region below the 18SrRNA. Gels 1, 3, 5, 7 and 8 show the various features of RNA degradation, whereas the corresponding gels 2, 4, 6, 9 and 10 (after adding N,N-dimethylacetamide to the preserving substances) have far better RNA quality.

N,N-Dimethylacetamide can thus not only be used alone, but can also be used as additive in small amounts in other preserving substances, improving the stabilization properties.

EXAMPLE 5

Long-Term Storage with N,N-dimethylacetamide

Rat renal tissue, which was frozen in liquid nitrogen after collection and then stored at −80° C., is used for this test. For each transition experiment, 20 to 50 mg of tissue is weighed and frozen, various non-cooled solutions (see Table 5) are added and the samples are stored for 3 days and 5 days at 25° C. Tissue that was frozen in liquid nitrogen after collection and then stored at −80° C. serves as control. Following transition, the RNA is isolated as described in example 1. The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 5. The mean values of determination in duplicate are given in each case.

TABLE 5

RNA yield and quality according to photometric measurement

| No. | Transition solution | Storage | OD260/ OD280 | RNA yield/μg |
|---|---|---|---|---|
| 1 | Frozen tissue | | 1.87 | 22.9 |
| 2 | N,N-Dimethylacetamide | 3 d 25° C. | 1.90 | 29.0 |
| 3 | | 5 d 25° C. | 1.91 | 26.0 |
| 4 | 50% N,N- | 3 d 25° C. | 1.93 | 27.9 |
| 5 | Dimethylacetamide + 50% methanol | 5 d 25° C. | 1.97 | 28.9 |
| 6 | 25% N,N- | 3 d 25° C. | 1.91 | 27.6 |
| 7 | Dimethylacetamide + 75% methanol | 5 d 25° C. | 1.98 | 23.1 |

Figure 2:
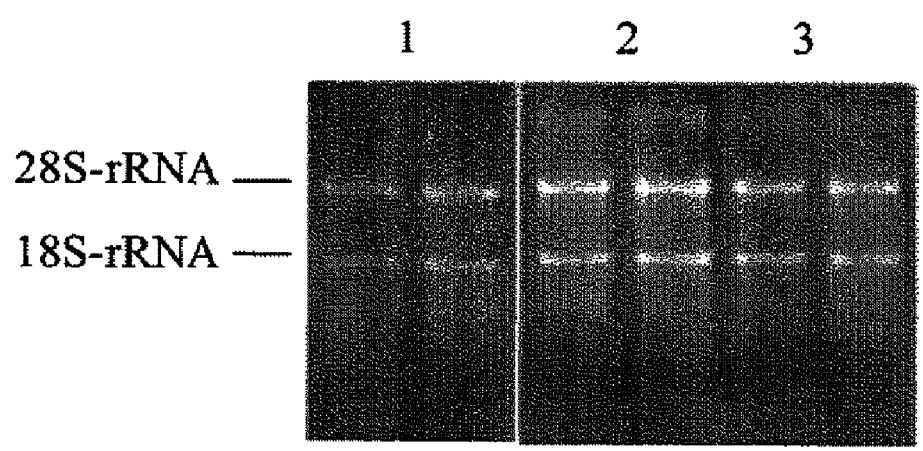
FIG. 2 shows the stabilization of RNA in rate renal tissue treated with N,N-dimethyl acetamide.

Additionally, as an example, the RNA isolated from samples 1 to 3 is analyzed on agarose gels stained with ethidium bromide. For this, for example 1.0% formaldehyde-agarose-MOPS gels are prepared. In each case, 5 μl of the eluate is used. The results are presented in FIG. 2. It can clearly be seen that addition of N,N-dimethylacetamide makes storage possible for a longer time at higher temperatures, without impairment of the yield, quality or integrity of the RNA.

EXAMPLE 6

Transition by Means of Mixtures with N,N-diethylacetamide

Rat liver tissue, which was frozen in liquid nitrogen after collection and then stored at −80° C., is used for this test. For each transition experiment, 20 to 50 mg of tissue is weighed and frozen, various non-cooled mixtures of N,N-dimethylacetamide and phenol (see Table 6) are added and the samples are stored for 1 day at room temperature or 3 days at 2-8° C. in the refrigerator. Following transition, the RNA is isolated as described in example 1. The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 6.

TABLE 6

RNA yield and quality according to photometric measurement

| Transition solution | Storage | OD260/ OD280 | RNA yield/ μg |
|---|---|---|---|
| 50% N,N-diethylacetamide + 50% ethanol | 3 d 2-8° C. | 1.92 | 33.3 |
| 75% N,N-diethylacetamide + 25% DMSO | 3 d 2-8° C. | 1.88 | 33.4 |
| 50% N,N-diethylacetamide + 50% DMSO | 3 d 2-8° C. | 1.95 | 30.5 |
| | 1 d RT | 1.86 | 39.0 |
| 25% N,N-diethylacetamide + 75% DMSO | 3 d 2-8° C. | 1.91 | 37.4 |
| | 1 d RT | 1.94 | 47.1 |
| 75% N,N-diethylacetamide + 25% acetone | 3 d 2-8° C. | 1.85 | 32.6 |
| 50% N,N-diethylacetamide + 50% acetone | 3 d 2-8° C. | 1.91 | 29.1 |
| 25% N,N-diethylacetamide + 75% acetone | 3 d 2-8° C. | 1.84 | 31.9 |
| 75% N,N-diethylacetamide + 25% diethylene glycol | 3 d 2-8° C. | 1.85 | 31.4 |
| 50% N,N-diethylacetamide + 50% diethylene glycol | 3 d 2-8° C. | 1.87 | 44.2 |
| 25% N,N-diethylacetamide + 75% diethylene glycol | 3 d 2-8° C. | 1.92 | 42.2 |
| 75% N,N-diethylacetamide + 25% ethylene glycol | 3 d 2-8° C. | 1.84 | 41.3 |
| 50% N,N-diethylacetamide + 50% 1,2-propanediol | 3 d 2-8° C. | 1.86 | 40.5 |
| 90% N,N-diethylacetamide + 10% methanol | 3 d 2-8° C. | 1.84 | 41.7 |
| | 1 d RT | 1.78 | 25.7 |
| 95% N,N-diethylacetamide + 5% N,N-dimethylacetamide | 3 d 2-8° C. | 1.88 | 35.2 |
| | 1 d RT | 1.88 | 38.7 |
| 25% N,N-diethylacetamide + 75% glycerol | 3 d 2-8° C. | 1.89 | 44.0 |
| 50% N,N-diethylacetamide + 50% glycerol | 3 d 2-8° C. | 1.91 | 42.8 |
| 25% N,N-diethylacetamide + 75% 1,3-propanediol | 3 d 2-8° C. | 1.88 | 22.1 |
| | 1 d RT | 1.94 | 25.1 |
| 50% N,N-diethylacetamide + 50% 1,3-propanediol | 3 d 2-8° C. | 1.84 | 40.5 |
| 75% N,N-diethylacetamide + 25% 1,3-propanediol | 3 d 2-8° C. | 1.91 | 39.9 |
| 25% N,N-diethylacetamide + 75% of 11.2M dihydroxyacetone solution (in water) | 3 d 2-8° C. | 1.82 | 36.2 |
| 25% N,N-diethylacetamide + 75% triethylene glycol | 3 d 2-8° C. | 1.86 | 45.5 |
| | 1 d RT | 1.85 | 38.8 |
| 50% N,N-diethylacetamide + 50% triethylene glycol | 3 d 2-8° C. | 1.82 | 36.9 |
| 75% N,N-diethylacetamide + 25% triethylene glycol | 3 d 2-8° C. | 1.84 | 45.9 |
| 25% N,N-diethylacetamide + 75% 1,2,6-hexanetriol | 3 d 2-8° C. | 2.03 | 38.0 |
| 50% N,N-diethylacetamide + 50% 1,2,6-hexanetriol | 3 d 2-8° C. | 1.93 | 39.4 |
| 25% N,N-diethylacetamide + 75% 1,5-pentanediol | 1 d RT | 2.02 | 43.2 |
| | 3 d 2-8° C. | 1.91 | 49.5 |
| 50% N,N-diethylacetamide + 50% 1,5-pentanediol | 1 d RT | 1.96 | 35.9 |
| | 3 d 2-8° C. | 1.94 | 46.7 |
| 75% N,N-diethylacetamide + 25% 1,5-pentanediol | 1 d RT | 1.91 | 41.3 |
| | 3 d 2-8° C. | 1.92 | 43.7 |
| 50% N,N-diethylacetamide + 50% 2,4-pentanediol | 3 d 2-8° C. | 1.97 | 32.2 |
| 75% N,N-diethylacetamide + 25% 2,4-pentanediol | 3 d 2-8° C. | 1.99 | 39.2 |
| 25% N,N-diethylacetamide + 75% 1-methoxy-2-propanol | 3 d 2-8° C. | 2.05 | 38.3 |
| 50% N,N-diethylacetamide + 50% 1-methoxy-2-propanol | 3 d 2-8° C. | 2.01 | 40.6 |
| 75% N,N-diethylacetamide + 25% 1-methoxy-2-propanol | 3 d 2-8° C. | 2.05 | 48.1 |

The results show that mixtures of N,N-diethylacetamide with various other preserving substances successfully stabilize RNA in transition experiments.

EXAMPLE 7

Long-Term Storage with N,N-diethylacetamide

Rat renal tissue, which was frozen in liquid nitrogen after collection and then stored at −80° C., is used for this test. For each transition experiment, 20 to 50 mg of tissue is weighed and frozen, various non-cooled solutions (see Table 7) are added and the samples are stored for 3 and 5 days at 25° C. Tissue frozen in liquid nitrogen after collection and then stored at −80° C. served as control. Following transition, the RNA is isolated as described in example 1.

The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 7.

TABLE 7

RNA yield and quality according to photometric measurement

| Transition solution | Storage | OD260/ OD280 | RNA yield/ μg |
|---|---|---|---|
| Frozen tissue | | 1.97 | 23.1 |
| 25% ethanol + 75% N,N-diethylacetamide | 3 d 25° C. 5 d 25° C. | 1.94 2.1 | 20.9 18.3 |
| 25% DMSO + 75% N,N-diethylacetamide | 3 d 25° C. 5 d 25° C. | 1.97 2.03 | 25.3 18.8 |
| 75% acetone + 25% N,N-diethylacetamide | 3 d 25° C. 5 d 25° C. | 1.96 2.06 | 15.8 17.6 |
| 25% diethylene glycol + 75% N,N-diethylacetamide | 3 d 25° C. 5 d 25° C. | 2.02 1.99 | 22.7 20.5 |
| 50% N,N-diethylacetamide + 50% 2,4-pentanediol | 3 d RT | 2.00 | 26.4 |
| 75% N,N-diethylacetamide + 25% 2,4-pentanediol | 3 d RT | 1.89 | 27.3 |
| 25% N,N-diethylacetamide + 75% 1-methoxy-2-propanol | 3 d RT | 1.99 | 21.1 |
| 50% N,N-diethylacetamide + 50% 1-methoxy-2-propanol | 3 d RT | 2.00 | 23.8 |
| 75% N,N-diethylacetamide + 25% 1-methoxy-2-propanol | 3 d RT | 1.96 | 20.5 |

The results show that solutions according to the invention and mixtures also make storage possible for a longer time at higher temperatures.

EXAMPLE 8

Stabilization of RNA in Cell Cultures

Figure 3:
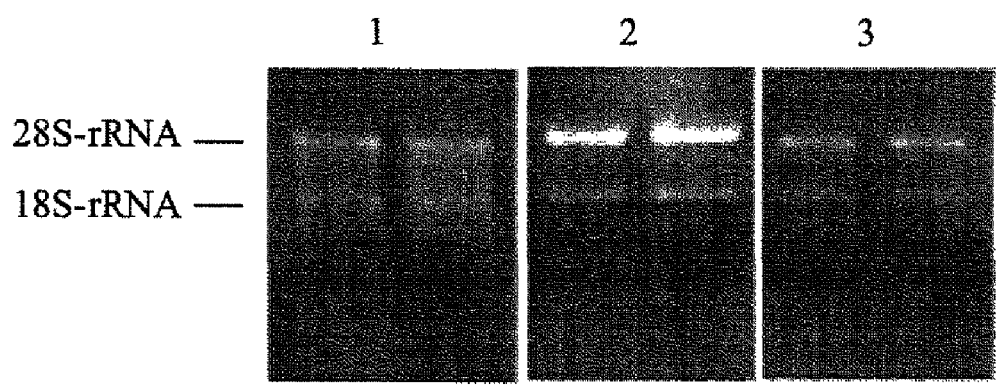
FIG. 3 shows the stability of RNA in rat renal cells treated with N, N-dimethyl acetamide.

Jurkat cell cultures are grown up to a density of 5.4×10e5 cells per ml. In each case 2 ml of this cell culture is centrifuged for each sample of the experiment and the medium is removed. The cell pellets are either dissolved in 500 μl N,N-diethylacetamide (sample 2) or are dissolved in 500 μl PBS and mixed with 5 ml of N,N-diethylacetamide (sample 3). The cells contacted with N,N-diethylacetamide are stored for 2 days at room temperature. 2 ml of the cell culture, which is centrifuged and, after removing the medium, is used directly for RNA isolation without prior storage, serves as control (sample 1). For RNA isolation, the cells are pelletized by centrifugation for 5 min at 1500×g and the supernatant is discarded. The pellets are in each case dissolved in 800 μl of buffer RLT from the company QIAGEN by vortexing. The lysate is mixed with 800 μl of 70% ethanol and in each case 700 μl of the mixture is applied twice on 2 separate RNeasy-Mini columns from the manufacturer QIAGEN and the lysate is driven through the membrane by centrifugation for 1 min at 10000×g. Subsequent RNA purification is carried out as described in example 1. The isolated RNA is analyzed on agarose gels stained with ethidium bromide. For this, for example 1.0% formaldehyde-agarose-MOPS gels are prepared. In each case, 5 μl of the eluate is used. The results are presented in FIG. 3. It can be seen that N,N-diethylacetamide also successfully stabilizes RNA in fresh cell cultures, both in the form of pellets, and in the form of suspensions.

EXAMPLE 9

Transition Time

Rat liver tissue, which was frozen in liquid nitrogen after collection and then stored at −80° C., is used for this test. For each transition experiment, 20 to 50 mg of tissue is weighed and frozen, N,N-dimethylacetamide is added and incubated in each case for 2.5 h, 6.5 h and 22 h at 2-8° C. in the refrigerator and at room temperature (see Table 8). Following transition, the RNA is isolated as described in example 1.

The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 8.

TABLE 8

RNA yield and quality according to photometric measurement

| No. | Storage temperature | Storage time | OD260/ OD280 | RNA yield/μg |
|---|---|---|---|---|
| 1 | 2-8° C. | 2.5 h | 1.91 | 45.9 |
| 2 | | 6.5 h | 1.97 | 43.0 |
| 3 | | 22 h | 1.94 | 40.0 |
| 4 | Room temperature | 2.5 h | 1.93 | 50.5 |
| 5 | | 6.5 h | 2.04 | 56.9 |
| 6 | | 22 h | 1.99 | 44.4 |

Figure 4:
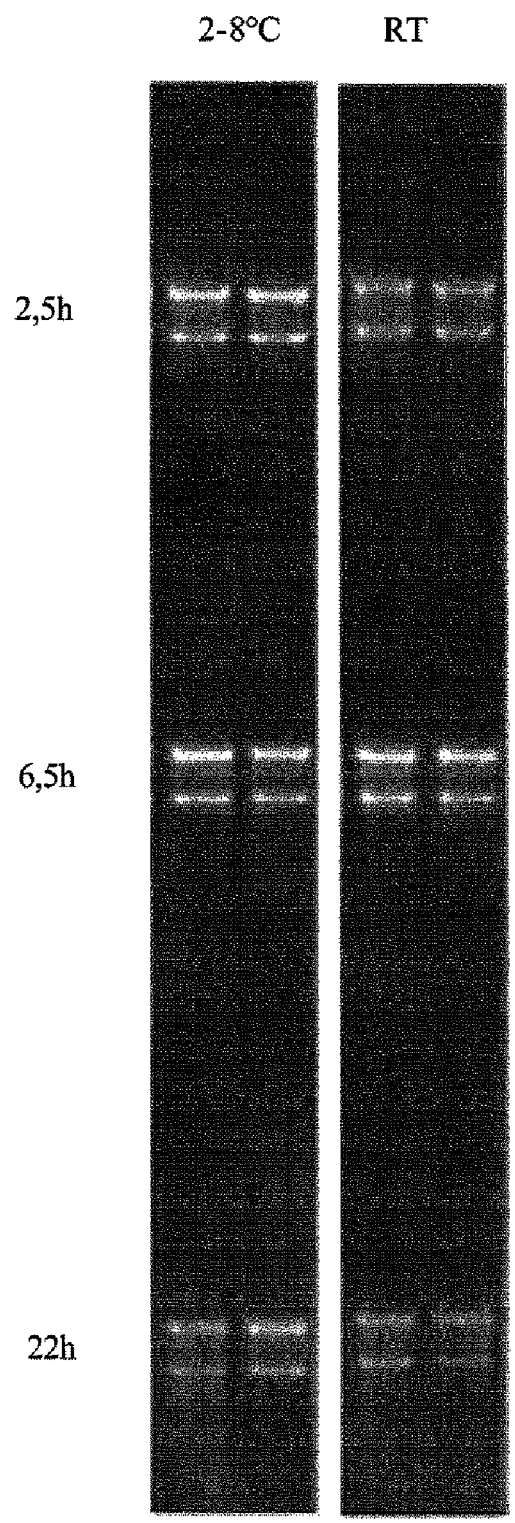
FIG. 4 shows the stability of RNA in rat liver tissue treated with dimethyl acetamide at 2 to 8° C. compared to room temperature.

The RNA isolated is analyzed on agarose gels stained with ethidium bromide. For this, for example 1.0% formaldehyde-agarose-MOPS gels are prepared. In each case, 5 μl of the eluate is used. The results are presented in FIG. 4 and show that transition in N,N-dimethylacetamide at various temperatures is also successful even after a short time.

EXAMPLE 10

Storage of the Samples Outside of the Transition Solution

Rat liver tissue, which was frozen in liquid nitrogen after collection and was stored at −80° C., is used for this test. A solution of 50% N,N-diethylacetamide and 50% DMSO is used as the transition solution. For the transition experiment, approx. 150 mg of tissue is weighed and frozen, and the aforementioned solution, precooled in the refrigerator to 2° C. to 8° C., is added. The sample is stored overnight at 2°-8° C. in the refrigerator.

After transition, the sample is taken out of the transition solution, divided up and the portions (approx. 10-30 mg) are stored dry at room temperature for 30 min (1), 45 min (2), 60 min (3), 90 min (4), 2 h 30 min (5) and 4 h 30 min (6). Then the RNA is isolated as described in example 1. Only single determinations are carried out for this test.

Figure 5:
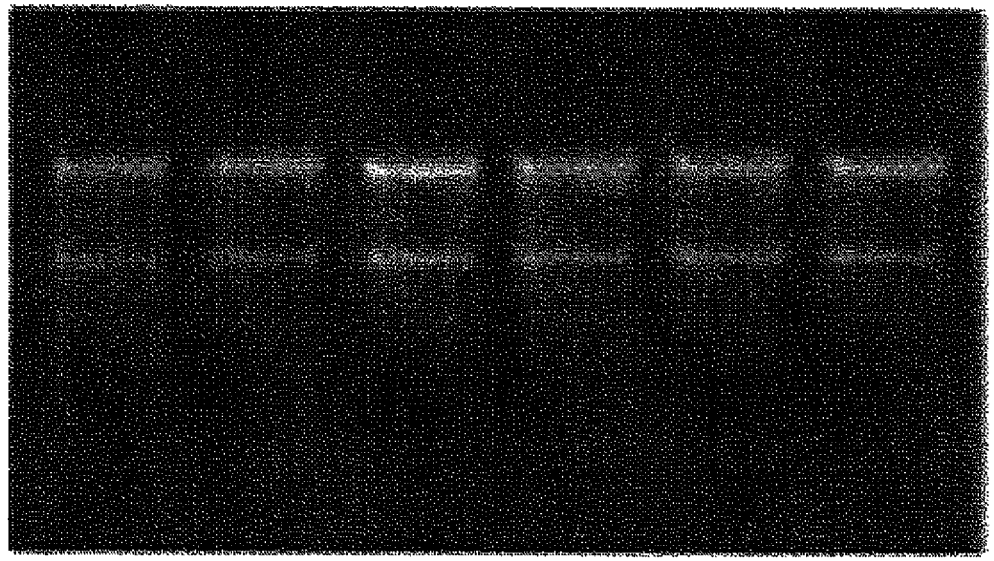
FIG. 5 demonstrates the storage stability of rat liver tissue treated with N,N-dimethyl acetamide for different time periods.

The RNA isolated is analyzed on agarose gels stained with ethidium bromide. For this, for example 1.0% formaldehyde-agarose-MOPS gels are prepared. In each case, 5 μl of the eluate is used. The results are presented in FIG. 5 and show that, after transition, the sample can also be kept for a prolonged period outside of the transition solution.

EXAMPLE 11

Stabilization of RNA in Fresh Tissue Samples

Fresh rat tissues are used for this experiment directly after collection. For each stabilization experiment, various solutions are added to approx. 20 to 50 mg of tissue and the samples are stored at various temperatures (see Table 9). Following storage, the RNA from liver is isolated as described in example 1. In the case of kidney and small intestine, the RNA is isolated as follows: for RNA isolation, the tissue is removed from the solutions after storage and, per 5 mg of kidney or per 10 mg of small intestine, 500 µl of a commercially available guanidinium isothiocyanate buffer, e.g. RLT buffer from QIAGEN, is added. The sample is homogenized by means of a ball mill, e.g. TissueLyzer from QIAGEN, for a period of 2×5 min at 25 Hz with 5 mm steel balls, so that the guanidinium isothiocyanate buffer lyses the cells in a manner known from the prior art and denatures the proteins that were released. Then the lysates are centrifuged at 14000 rpm for 3 min. 500 µl, representing 5 mg of tissue, is taken from the supernatant. 1 volume (500 µl) of 70% ethanol is added to these samples, mixing by repeated pipetting or by vortexing for a period of approx. 5 s. The lysate is then applied in a commercially available silica membrane-containing 96-well plate, e.g. RNeasy96 plate from the company QIAGEN, and is driven through the membrane by centrifugation (4 min at 6000 rpm). The RNA remains bound to the membrane and is then washed with a first commercially available washing buffer containing guanidinium isothiocyanate, for example with buffer RW1 from QIAGEN. Then, for enzymatic removal of any bound total DNA, DNAseI in a suitable buffer is applied to the column and incubated for 15 min at room temperature for the purpose of degradation of the bound DNA. Next, it is washed again with a first commercially available washing buffer containing guanidinium isothiocyanate, for example with buffer RW1 from QIAGEN, and then with a second washing buffer containing Tris or Tris and alcohol, e.g. buffer RPE from QIAGEN. In each case the washing buffer is driven through the membrane by centrifugation (4 min at 6000 rpm). Washing with the second washing buffer containing Tris or Tris and alcohol is repeated, simultaneously drying the membrane by centrifugation (10 min 6000 rpm). For elution, 50 µl of RNase-free water is pipetted onto the membrane, to remove the purified RNA from the membrane. After incubation for 1 minute at a temperature in the range 10-30° C., the eluate is driven through the membrane by centrifugation (1 min at 10000×g) and the elution step is repeated once more for complete elution. The amount of total RNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 9.

TABLE 9

RNA yield and quality according to photometric measurement

| No. | Transition solution | Tissue | Storage | OD260/OD280 | RNA yield/µg |
|---|---|---|---|---|---|
| 1 | Frozen tissue | | | | |
| 2 | 50% N,N-diethylacetamide + | Kidney | 1 d 37° C. | 2.06 | 11.2 |
| 3 | 50% DMSO | Kidney | 7 d 2-8° C. | 2.08 | 17.9 |
| 4 | | Small intestine | 7 d 25° C. | 1.98 | 13.1 |
| 5 | 25% N,N-diethylacetamide + | Kidney | 1 d 37° C. | 2.08 | 12.0 |
| 6 | 75% DMSO | Kidney | 7 d 25° C. | 2.11 | 14.1 |
| 7 | | Kidney | 3 d 2-8° C. | 2.08 | 11.0 |
| 8 | | Kidney | 7 d 2-8° C. | 2.09 | 19.4 |
| 9 | | Small intestine | 7 d 25° C. | 2.12 | 20.3 |
| 10 | | Small intestine | 7 d 2-8° C. | 2.08 | 29.6 |
| 11 | 5% N,N-dimethylacetamide + 95% ethanol + acetic acid (40 µl to 20 ml total volume) | Liver | 3 d 25° C. | 1.926 | 45.7 |
| 12 | 75% N,N-diethylacetamide + 25% diethylene glycol | Liver | 3 d 25° C. | 1.99 | 59.3 |
| 13 | 25% N,N-diethylacetamide + 75% 2,4-pentanediol | Liver | 3 d 25° C. | 1.89 | 60.3 |
| 14 | 25% N,N-diethylacetamide + 75% 1,2,3-propanetriol | Liver | 3 d 25° C. | 2.1 | 64.4 |

Figure 6:
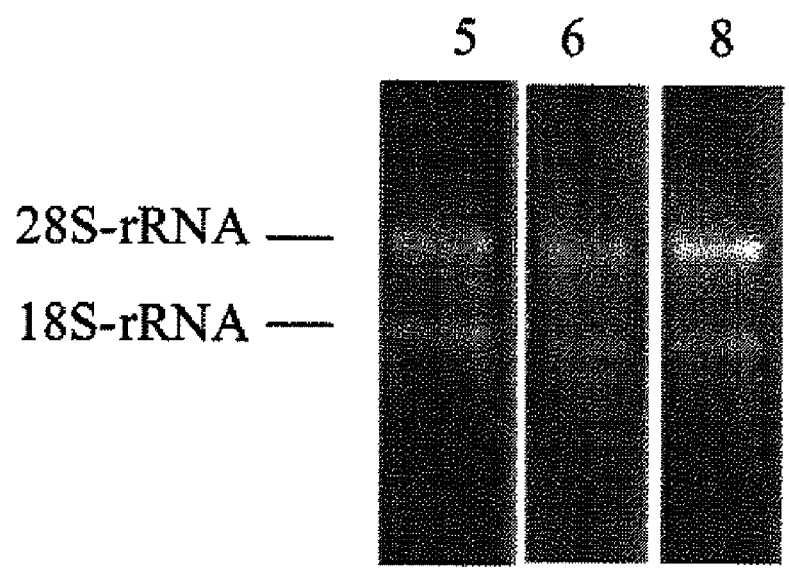
FIG. 6 shows the stabilization of RNA in fresh rat tissue treated with N,N-dimethyl acetamide.

In addition, as an example, the RNA isolated from some samples is analyzed on agarose gels stained with ethidium bromide. For this, for example 1.0% formaldehyde-agarose-MOPS gels are prepared. In each case, 5 µl of the eluate is used. The results are presented in FIG. 6 and show that the solutions according to the invention can also successfully stabilize RNA in fresh tissue, and can be stored for long periods at high temperatures.

EXAMPLE 12

Stabilization of DNA in Fresh Tissue Samples

Mixtures of N,N-diethylacetamide and DMSO were added to rat renal tissue immediately after organ removal and the samples were stored at various temperatures (see Table 10). Following storage, the DNA is isolated from the stored samples. For DNA isolation, after storage the tissue is removed from the solutions and 180 µl of buffer ALT from QIAGEN is added per 10 mg of tissue. The sample is homogenized by means of a ball mill, e.g. TissueLyzer from QIAGEN, for a period of 30 s at 25 Hz with 5 mm steel balls, and then centrifuged for 15 seconds at 14000×g. After adding 120 µl of protease K solution (manufacturer QIAGEN), the lysates are incubated for 2 hours at 55° C. with shaking. After incubation, 4 µl of RNase A (100 mg/ml) is added, mixed and the mixture is incubated for 2 min at room temperature. After incubation, 300 µl of a commercially available lysis buffer containing guanidinium hydrochloride, such as buffer AL from QIAGEN, is added and the samples are mixed thoroughly by vortexing. Incubation takes place at 70° C. for 10 min. After mixing with 300 µl of 100% ethanol, the samples are applied on a silica membrane-containing 96-well plate (DNeasy 96 plate from QIAGEN) and the lysate is driven through the membrane by centrifugation for 10 min at 6000 rpm. The DNA remains bound to the membrane and is washed first with a first commercially available washing buffer containing guanidinium hydrochloride, for example with buffer AW1 from QIAGEN, and then with a second alcohol-containing washing buffer, e.g. buffer AW2 from QIAGEN. In each case the washing buffers are driven through the membrane by centrifugation (5 min at 6000 rpm). Following this, the plate is incubated for 10 min at 70° C. Elution of the DNA is carried out by applying 200 µl of elution buffer AE (QIAGEN) preheated to 70° C. After incubation for one minute, the elution buffer is driven through the membrane by centrifugation (5 min at 6000 rpm) and elution is repeated. The amount of total DNA isolated is determined, after dilution in water, by photometric measurement of light absorption at a wavelength of 260 nm. The quality of the RNA thus obtained is determined by photometric determination of the ratio of light absorption at 260 nm to that at 280 nm. The results of the isolation operations are shown in Table 10.

TABLE 10

DNA yield and quality according to photometric measurement

| Transition solution | Storage | OD260/OD280 | RNA yield/µg |
|---|---|---|---|
| 50% DMSO + | 1 d 37° C. | 1.96 | 17.9 |
| 50% N,N-diethylacetamide | 3 d 25° C. | 1.93 | 12.8 |
| | 3 d 2-8° C. | 1.97 | 15.0 |
| | 7 d 25° C. | 2.01 | 19.84 |
| | 7 d 2-8° C. | 1.99 | 24.9 |
| 75% DMSO + | 1 d 37° C. | 1.97 | 17.5 |
| 25% N,N-diethylacetamide | 3 d 25° C. | 1.96 | 13.3 |
| | 3 d 2-8° C. | 1.97 | 13.21 |
| | 7 d 25° C. | 1.98 | 17.61 |
| | 7 d 2-8° C. | 2.03 | 26.9 |

The results show that the solutions according to the invention can also successfully stabilize DNA in fresh tissue, with storage over long periods at high temperatures being possible.

EXAMPLE 13

Histological Analysis of Stabilized Tissues

In each case 1 ml of 25% N,N-diethylacetamide+75% DMSO was added to rat liver and renal tissue immediately after organ removal, storing for 1 day at 25° C. in the incubator. After storage, the pieces of tissue are taken out of the solutions, transferred to plastic cassettes and incubated according to usual protocols in an increasing ethanol series, and in xylene, and embedded in paraffin. Using a microtome, sections are prepared from the tissue embedded in paraffin, and these are stained with hematoxylin-eosin on the microscope slide by the usual methods. The stained tissue sections are examined by light microscopy, and it is found that the solution is able to preserve the morphology of the tissue.

EXAMPLE 14

Stabilization of Proteins in Fresh Tissue Samples

Figure 7:
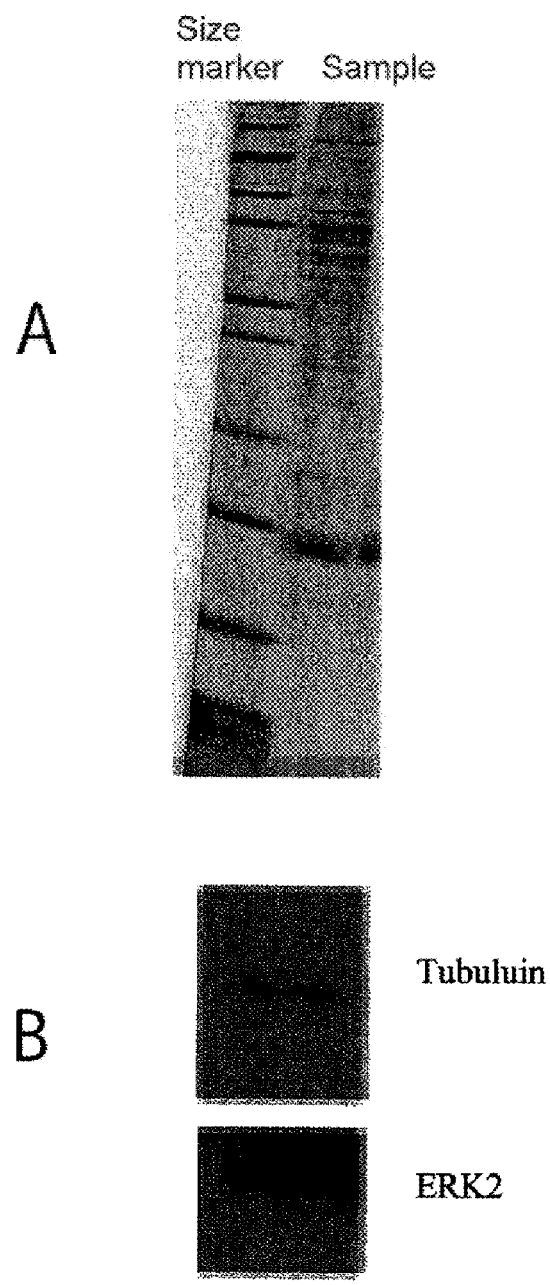
FIGS. 7 A and B show the stabilization of DNA from fresh rate renal tissue treated with N, N-dimethyl acetamide.

Immediately after organ removal, 1 ml of 25% N,N-diethylacetamide+75% DMSO was added to rat liver tissue and the sample was stored for 3 days at room temperature. Following storage, a protein extract is prepared from the stored sample. For preparation of the protein extract, after storage the tissue is removed from the solutions and 400 µl of a usual extraction buffer, in this case in a composition of 8M urea, 100 mM sodium dihydrogen phosphate and 10 mM Tris, pH 8.0, is added per 10 mg of tissue, and the sample is homogenized by means of a ball mill, e.g. the TissueLyzer from QIAGEN. The resultant lysate is centrifuged for 15 s at the maximum speed (e.g. approx. 20000×g) in order to pelletize undissolved constituents. The protein-containing supernatant is drawn off and the protein concentration is determined by a Bradford test. 1.5 µg of protein is separated on an SDS-polyacrylamide gel by the usual method and on the one hand the gel is stained with Coomassie according to the usual method and on the other hand a second gel is blotted on a nitrocellulose membrane using a semidry-blotting apparatus according to the manufacturer's instructions. The membrane is saturated with milk powder according to the prior art and hybridized with an ERK2-specific antibody and a tubulin-specific antibody according to the manufacturer's instructions, and immunodetection is carried out. The results are presented in FIG. 7, and show that the proteins are stabilized by the composition according to the invention at room temperature in tissues.

The invention claimed is:
1. A method of stabilizing cells and biomolecules present in a biological sample, having the following steps:
    (a) providing a biological sample comprising cells and biomolecules;
    (b) contacting the biological sample with a composition having a preserving substance according to the following structural formula:

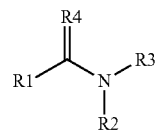

in which R1 is a hydrogen residue or a methyl residue, R2 and R3 are identical or different hydrocarbon residues with a length of the carbon chain of 1-20, and R4 is an oxygen, sulfur or selenium atom, to produce a mixture, wherein stabilization of the biological sample in the mixture occurs without fixation or crosslinking of the biomolecules, wherein the preserving substance is the only preserving substance in the composition and wherein decomposition, modification, induction or change of activity of the biomolecules in the mixture is inhibited, and wherein the preserving substance is the only preserving substance in the mixture.
2. The method as claimed in claim 1, wherein the biological sample is a frozen biological sample.
3. The method as claimed in claim 1, wherein the biological sample is a non frozen biological sample.
4. The method as claimed in claim 1, wherein the biological sample comprising cells is a material selected from the group comprising body fluids, blood, leukocyte fractions, crusta phlogistica, sputum, saliva, urine, semen, feces, forensic samples, smears, aspirates, biopsies, tissue samples, tissue parts and organs.

5. The method as claimed in claim 1, wherein the preserving substance is selected from the group comprising N,N-dimethylacetamide, N,N-diethylacetamide, N,N-dimethylformamide, N,N-diethylformamide, N,N-dimethylthioformamide and N,N-diethylthioformamide.

6. The method as claimed in claim 1, wherein the biological sample is in addition brought in contact with one or more substances selected from the group consisting of buffers, osmotically active substances, chelators, reducing agents, and agents for improving the visibility of the cell nucleus.

7. The method as claimed in claim 1, wherein the contacting of the biological sample with the composition takes place at a temperature in the range from −80° C. to +80° C.

8. The method as claimed in claim 1, further comprising the following step: (c) storing the mixture at a temperature in the range from −80° C. to +80° C.

9. The method as claimed in claim 8, wherein in step (c), storing occurs at conditions selected from
   (i) 2° C. to +80° C.,
   (ii) 8° C. to +80° C.
   (iii) 18° C. to +80° C. and
   (iv) room temperature.

10. The method as claimed in claim 8, wherein in step (c), the storing occurs over a period selected from
   (i) at least one day,
   (ii) at least two days and
   (iii) at least three days.

11. The method as claimed in claim 1, wherein the biomolecules are nucleic acids.

12. A method of analysis of a biological sample, comprising the steps of:
   (a) providing a biological sample comprising cells and biomolecules;
   (b) contacting the biological sample with a composition having a preserving substance according to the following structural formula:

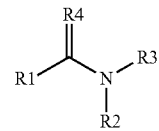

in which R1 is a hydrogen residue or a methyl residue, R2 and R3 are identical or different hydrocarbon residues with a length of the carbon chain of 1-20, and R4 is an oxygen, sulfur or selenium atom, to produce a mixture, wherein stabilization of the biological sample in the mixture occurs without fixation or crosslinking of the biomolecules, wherein the preserving substance is the only preserving substance in the composition and wherein decomposition, modification, induction or change of activity of the biomolecules in the stabilized sample is inhibited, wherein the preserving substance is the only preserving substance in the mixture;
   (c) storing the mixture at a temperature in the range from −80° C. to +80° C.;
   (d) histological-morphological analysis of the mixture; and/or
   (e) analysis of the biomolecules in the mixture.

13. The method as claimed in claim 12, wherein the analysis for step(s) (d) and/or (e) comprises isolation of the biomolecules from the mixture.

* * * * *